(12) United States Patent
Nakamura et al.

(10) Patent No.: US 9,040,661 B2
(45) Date of Patent: May 26, 2015

(54) SUPPORT FOR AFFINITY CHROMATOGRAPHY AND METHOD FOR ISOLATING IMMUNOGLOBULIN

(75) Inventors: Satoshi Nakamura, Minato-ku (JP); Tetsuo Fukuta, Minato-ku (JP); Yusuke Okano, Minato-ku (JP); Tomonori Shiotani, Minato-ku (JP); Kouji Tamori, Minato-ku (JP); Yu Otani, Minato-ku (JP); Shun-Cheng Li, London (CA); Xing Li, London (CA); Courtney Voss, London (CA)

(73) Assignees: JSR Corporation, Minato-ku (JP); THE UNIVERSITY OF WESTERN ONTARIO, London (CA)

( * ) Notice: Subject to any disclaimer, the term of this patent is extended or adjusted under 35 U.S.C. 154(b) by 0 days.

(21) Appl. No.: 13/996,978

(22) PCT Filed: Dec. 20, 2011

(86) PCT No.: PCT/JP2011/079568
§ 371 (c)(1),
(2), (4) Date: Sep. 5, 2013

(87) PCT Pub. No.: WO2012/086660
PCT Pub. Date: Jun. 28, 2012

(65) Prior Publication Data
US 2014/0005357 A1    Jan. 2, 2014

Related U.S. Application Data

(60) Provisional application No. 61/425,412, filed on Dec. 21, 2010, provisional application No. 61/425,617, filed on Dec. 21, 2010.

(30) Foreign Application Priority Data

Dec. 22, 2010 (JP) .................... 2010-285492

(51) Int. Cl.
*C07K 1/22* (2006.01)
*C07K 17/08* (2006.01)
*C07K 16/06* (2006.01)

(52) U.S. Cl.
CPC ............ *C07K 1/22* (2013.01); *C07K 16/065* (2013.01); *C07K 17/08* (2013.01)

(58) Field of Classification Search
None
See application file for complete search history.

(56) References Cited

U.S. PATENT DOCUMENTS

| | | | |
|---|---|---|---|
| 5,084,559 A | 1/1992 | Profy | |
| 5,260,373 A | 11/1993 | Profy et al. | |
| 5,831,012 A | 11/1998 | Nilsson et al. | |
| 6,013,763 A | 1/2000 | Braisted et al. | |
| 6,197,927 B1 | 3/2001 | Braisted et al. | |
| 6,534,628 B1 | 3/2003 | Nilsson et al. | |
| 6,740,734 B1 | 5/2004 | Nilsson et al. | |
| 6,831,161 B1 | 12/2004 | Uhlen et al. | |
| 7,485,704 B2 | 2/2009 | Fahrner et al. | |
| 7,709,209 B2 | 5/2010 | Hober et al. | |
| 7,834,158 B2 | 11/2010 | Hober | |
| 8,198,404 B2 | 6/2012 | Hober | |
| 8,354,510 B2 | 1/2013 | Hober et al. | |
| 2005/0100970 A1 | 5/2005 | Uhlen et al. | |
| 2006/0194950 A1 | 8/2006 | Hober et al. | |
| 2009/0099344 A1 | 4/2009 | Fahrner et al. | |
| 2010/0105879 A1 | 4/2010 | Katayose et al. | |
| 2010/0221844 A1* | 9/2010 | Bian et al. ............... 436/501 |
| 2010/0286373 A1 | 11/2010 | Majima et al. | |
| 2012/0208234 A1 | 8/2012 | Yoshida et al. | |
| 2012/0238724 A1 | 9/2012 | Hober | |

FOREIGN PATENT DOCUMENTS

| | | | |
|---|---|---|---|
| CA | 2 347 960 | 4/2000 | |
| CN | 1319988 | * 6/2005 | ............ C07K 14/00 |
| CN | 1634990 | * 7/2005 | ............ C07K 14/00 |
| CN | 101632019 | 1/2010 | |
| CN | 101775069 | 7/2010 | |
| EP | 1992692 A1 | 11/2008 | |
| EP | 2128616 A1 | 12/2009 | |
| EP | 2202310 A2 | 12/2009 | |

(Continued)

OTHER PUBLICATIONS

Linhult, M., "Protein engineering to explore and improve affinity ligands", Royal Institute of Technology, Department of Biotechnology, Total 69 Pages, (2003).

(Continued)

*Primary Examiner* — Maury Audet
(74) *Attorney, Agent, or Firm* — Oblon, McClelland, Maier & Neustadt, L.L.P.

(57) ABSTRACT

Provided are a support for affinity chromatography which has excellent alkali resistance, and a method for isolating immunoglobulin. A support for affinity chromatography, containing an immobilized protein ligand represented by the following formula (1):

$$R\text{—}R^2 \qquad (1)$$

wherein R represents a polypeptide consisting of 4 to 30 amino acid residues that contains an amino acid sequence represented by ATK or ASK; and $R^2$ represents a polypeptide consisting of 50 to 500 amino acid residues containing an immunoglobulin-binding domain consisting of an amino acid sequence represented by SEQ ID NO: 1 or SEQ ID NO: 2, the partial sequence thereof, or an amino acid sequence having 70% or more identity to these sequences; with the proviso that a terminus at which $R^2$ binds to R is C-terminus or N-terminus of the immunoglobulin-binding domain.

21 Claims, 1 Drawing Sheet

(56) References Cited

FOREIGN PATENT DOCUMENTS

| | | |
|---|---|---|
| EP | 2 202 310 | 6/2010 |
| JP | 6 281638 | 10/1994 |
| JP | 2006-304633 | 11/2006 |
| JP | 2007-252368 | 10/2007 |
| JP | 2008-214350 | 9/2008 |
| JP | 2008-241560 | 10/2008 |
| JP | 2010-156687 | 7/2010 |
| WO | 95 19374 | 7/1995 |
| WO | 2007/097361 | 8/2007 |
| WO | 2008/117638 | 10/2008 |
| WO | 2010/035756 | 4/2010 |
| WO | 2010 035756 | 4/2010 |
| WO | 2010/110288 | 9/2010 |

OTHER PUBLICATIONS

International Search Report Issued May 3, 2012 in Related Application PCT/CA11/001370 Filed Dec. 21, 2011.
U.S. Appl. No. 13/997,015, filed Jun. 21, 2013, Li, et al.
International Search Report mailing date Mar. 6, 2012, corresponding application No. PCT/JP2011/079568.

\* cited by examiner

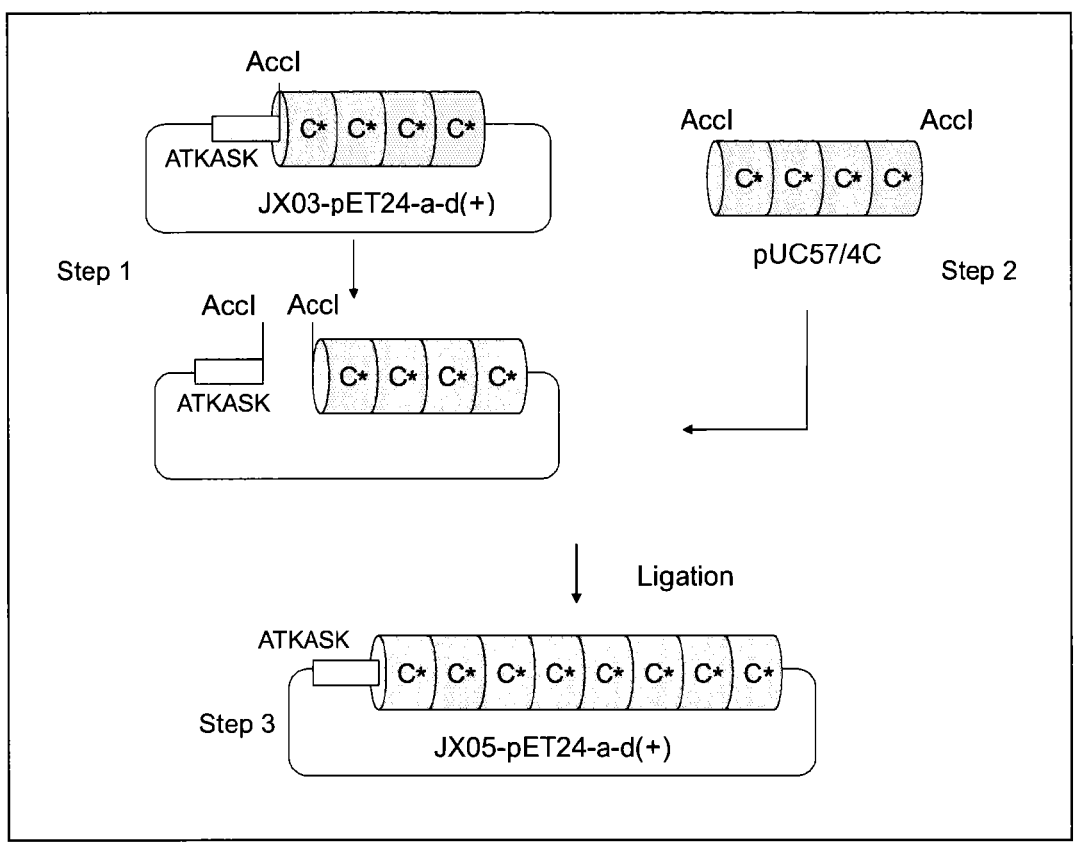

SUPPORT FOR AFFINITY CHROMATOGRAPHY AND METHOD FOR ISOLATING IMMUNOGLOBULIN

FIELD OF THE INVENTION

The present invention relates to a support for affinity chromatography, and a method for isolating immunoglobulin. Particularly, the present invention relates to a support for affinity chromatography to which a particular ligand useful for purification of immunoglobulin is bound, and a method for isolating immunoglobulin.

BACKGROUND OF THE INVENTION

Affinity chromatography is chromatography using a column filled with a ligand-immobilized support obtained by immobilizing a substance that specifically binds to a substance for separation and purification (ligand), on an insoluble support. Affinity chromatography is used for, for example, separation and purification of biological substances such as proteins and nucleic acids (JP-A-H06-281638).

As the support for affinity chromatography, for example, particles obtained by crosslinking sugar chains (representatively agarose gel), or particles containing a synthetic polymer as a main component, are used.

Now, for use in bioseparation, a support is usually used repeatedly. However, since there would be residual trace amounts of contaminants in the support even after purification operation, washing step of removing the contaminants to restore the support to the original state is carried out while the support is repeatedly used. In the washing step, usually an operation known as cleaning in place (CIP) is carried out, and a reagent capable of eluting contaminants from the support (CIP agent) is used. Examples of such reagents include alkaline liquids such as sodium hydroxide. In the case of using sodium hydroxide, contaminants such as microorganisms, proteins, lipids and nucleic acids can be effectively removed.

However, when contaminants are removed from the support by using an alkaline liquid, the support is exposed to an alkaline condition. For a support for affinity chromatography using a protein as a ligand, such an alkaline condition is severe and may cause a decrease of capacity due to decreased stability of the ligand. Particularly, most of the supports for affinity chromatography in which the ligand is a polypeptide such as protein A are unstable under the severe alkaline condition.

CITATION LISTING

Patent Document

Patent Document 1: JP-A-H06-281638

SUMMARY OF THE INVENTION

An embodiment of the present invention is a support for affinity chromatography, wherein a protein ligand represented by the following formula (1) is immobilized:

$$R\text{—}R^2 \qquad (1)$$

wherein R represents a polypeptide consisting of 4 to 30 amino acid residues containing an amino acid sequence represented by ATK or ASK;

and wherein $R^2$ represents a polypeptide consisting of 50 to 500 amino acid residues that contains an immunoglobulin-binding domain consisting of an amino acid sequence represented by SEQ ID NO: 1 or SEQ ID NO: 2, the partial sequence thereof, or an amino acid sequence having 70% or more identity to these sequences;

with the proviso that a terminus at which $R^2$ binds to R is C-terminus or N-terminus of the immunoglobulin-binding domain.

In an embodiment of the support for affinity chromatography described above, the protein ligand represented by the formula (1) can be immobilized on the support via epoxy group ring-opening reaction between an amino group or a thiol group in the ligand and an epoxy group in the support.

Another aspect of the present invention is a method for isolating immunoglobulin, the method includes:

applying a sample containing immunoglobulin in the support for affinity chromatography described above, to adsorb the immunoglobulin to the support; and eluting the immunoglobulin from the support.

In an embodiment of the method of the present invention, the support for affinity chromatography used in the step of eluting the immunoglobulin can be used again for the isolation of immunoglobulin by the above-mentioned method after washing the support with an alkaline liquid.

BRIEF DESCRIPTION OF DRAWINGS

FIG. 1 shows a procedure for construction of JX-05pET24-a-d(+) where the depicted amino acid sequence  ATKASK is identified by SEQ ID NO: 44).

DETAILED DESCRIPTION OF THE INVENTION

According to the present specification, the term "protein" means all molecules which have a peptide structural unit, and represents a concept including, for example, partial fragments of naturally occurring proteins, and variants obtained by artificially modifying the amino acid sequences of naturally occurring proteins. Furthermore, the "immunoglobulin-binding domain" means a functional unit of a polypeptide showing an immunoglobulin-binding activity by itself, and the "immunoglobulin-binding protein" means a protein which shows specific affinity to an immunoglobulin and includes the "immunoglobulin-binding domain." The term "immunoglobulin binding" means binding to a region other than the complementarity determining region (CDR) of an immunoglobulin molecule, particularly the Fc fragment.

Protein A as used in the present specification is Protein A which is a cell wall component of *Staphylococcus aureus*.

In the present specification, the sequence identity between base sequence and amino acid sequence is calculated by Lipman-Pearson method (Science, 227, 1435, (1985)). Specifically, by using a search homology program of genetic information processing software GENETYX-Win (Ver. 5.1.1; Software Development Co., Ltd.), the sequence identity is calculated by performing the analysis taking the unit size to compare (ktup) parameter as 2.

An object of the present invention is to provide a support for affinity chromatography showing excellent alkali resistance, and a method for isolating immunoglobulin.

The support for affinity chromatography of the present invention shows excellent alkali resistance, and therefore shows high resistance to the washing under an alkaline condition. Furthermore, when the support for affinity chromatography is used for, for example, purification of immunoglobulin, since the dynamic binding capacity for immunoglobulin is not easily decreased even if the support is repeatedly used, the purification of immunoglobulin can be carried out at low cost.

The support for affinity chromatography according to an embodiment of the present invention is characterized in that a protein ligand represented by the following formula (1) is immobilized on the support.

Wherein

R represents a polypeptide consisting of 4 to 30 amino acid residues containing ATK or ASK; and $R^2$ represents a polypeptide consisting of 50 to 500 amino acid residues that contains an immunoglobulin-binding domain consisting of an amino acid sequence represented by SEQ ID NO: 1 or SEQ ID NO: 2, the partial sequence thereof, or an amino acid sequence having 70% or more identity to these sequences, with the proviso that a terminus at which $R^2$ binds to R is C-terminus or N-terminus of the immunoglobulin-binding domain.

1. Support for Affinity Chromatography

1.1 Support

1.1.1. Constitution

The shape of the support can be in the form of particles and such particles may be porous or non-porous. A particulate support can be used as a packed bed, or can be used in a suspension form. Suspension forms include a fluidized bed (expanded bed) and a product known as a sheer suspension, and particles can freely be moved about therein. In the case of a monolith, a packed bed and a fluidized bed, the order of separation steps generally complies with conventional chromatographic methods based on concentration gradients. In the case of the sheer suspension, a batch method is used. Preferably, the support is a filler. Alternatively, the support may be in the form of a chip, a capillary or a filter.

The support for affinity chromatography according to the present embodiment has a particle size (mean volume diameter) of preferably 20 µm to 200 µm; in the case where the support is a synthetic polymer, more preferably 20 µm to 80 µm, and furthermore preferably 30 µm to 60 µm; and in the case where the support is a polysaccharide, more preferably 50 µm to 200 µm, and furthermore preferably 60 µm to 150 µm. When the particle size is less than 20 µm, the column pressure becomes higher at a high flow rate, and thus the support cannot withstand the practical use. When the particle size exceeds 200 µm, there may be a case where the amount of immunoglobulin that binds to the support for affinity chromatography (binding capacity) is decreased. Meanwhile, the "particle size" according to the present invention is the mean volume diameter of the support measured by a laser diffraction scattering type particle size distribution analyzer.

The support for affinity chromatography according to the present embodiment is preferably porous, and has a specific surface area of 50 $m^2/g$ to 150 $m^2/g$, and more preferably 80 $m^2/g$ to 130 $m^2/g$. Here, when the specific surface area is less than 50 $m^2/g$, there may be a case where the binding capacity is decreased. On the other hand, when the specific surface area exceeds 150 $m^2/g$, the strength of the support is inferior and the support is broken at a high flow rate, and as a result, there may be a case where the pressure inside the column is increased. The "specific surface area" according to the present invention is the value obtained by dividing the surface area of fine pores having a pore size of 10 nm to 5,000 nm as determined by using a mercury porosimeter, by the dry weight of the particles.

The support for affinity chromatography according to the present embodiment has a volume mean pore size of preferably 100 nm to 1400 nm; in the case where the support is a synthetic polymer, more preferably 100 nm to 400 nm, and furthermore preferably 200 nm to 300 nm; and in the case where the support is a polysaccharide, more preferably 500 nm to 1400 nm, and furthermore preferably 800 nm to 1200 nm. Here, when the volume mean pore size is less than 100 nm, there may be a case where the decrease of the binding capacity at a high flow rate becomes remarkable. On the other hand, when the volume mean pore size exceeds 1400 nm, there may be a case where the binding capacity is decreased, irrespective of the flow rate. The "volume mean pore size" according to the present invention is the volume mean pore size of fine pores having a pore size of 10 nm to 5,000 nm as determined by using a mercury porosimeter.

When the particle size, specific surface area and pore size distribution in the ranges described above are satisfied, the balance between a gap between the particles, which serve as flow path of the solution to be purified, the relatively large pore size in the particles, and the surface area for binding to the molecules to be purified is optimized, and the binding capacity at a high flow rate is maintained at a high level.

The material of the support is, for example, a polymer having a hydrophilic surface, and for example, a polymer having a hydroxyl group (—OH), a carboxyl group (—COOH), an aminocarbonyl group (—$CONH_2$, or N-substituted type), an amino group (—$NH_2$, or substituted type), an oligo or a polyethyleneoxy group at the outer surface (and if available, also at the inner surface). The polymer according to an embodiment is a synthetic polymer such as polymethacrylate, polyacrylamide, or a styrene-divinylbenzene copolymer. Such synthetic polymer can be easily produced by a known method (see a method described in, for example, J. MATER. CHEM., 1991, 1 (3), 371-374). Alternatively, commercially available products such as TOYOPEARL (Tosoh Corp.) may also be used. The polymer according to another embodiment is a polysaccharide such as dextran, starch, cellulose, pullulan, or agarose. Such polysaccharides are easily produced by known methods (see, for example, a method described in Japanese Patent No. 4081143). Alternatively, commercially available products such as SEPHAROSE (GE Healthcare Bioscience Corp.) may also be used. In other embodiments, for example, an inorganic support of silica, zirconium oxide may also be used.

One specific example of porous particles used as the support in the support for affinity chromatography according to the present embodiment is, for example, porous organic polymer particles which contains a copolymer of 20% to 50% by mass of a crosslinkable vinyl monomer, 3% to 80% by mass of an epoxy group-containing vinyl monomer, and 20% to 80% by mass of a diol group-containing vinyl monomer, and which has a particle size of 20 µm to 80 µm, a specific surface area of 50 $m^2/g$ to 150 $m^2/g$, and a volume mean pore size of 100 nm to 400 nm.

Meanwhile, the intrusion volume (pore volume) of fine pores having a pore size of 10 nm to 5,000 nm, in the case where the support for affinity chromatography according to the present embodiment is measured with a mercury porosimeter, is preferably 1.3 mL/g to 7.0 mL/g, in the case where the support is a synthetic polymer, is more preferably 1.3 mL/g to 2.5 mL/g, and in the case where the support is a polysaccharide, is more preferably 3.0 mL/g to 6.0 mL/g.

1.1.2. Binding to Ligand

As the method for binding to ligand, the binding can be carried out by using a general method of immobilizing a protein on a support. Examples include a method of using a support having a carboxyl group, and activating this carboxyl group with N-Hydroxysuccinimide to react with an amino group of a ligand; a method of using a support having an amino group or a carboxyl group, and subjecting the support to react with a carboxyl group or an amino group of a ligand in the presence of a dehydration condensing agent such as a water-soluble carbodiimide, to thereby form an amide bond; a method of using a support having a hydroxyl group, and activating the support with a cyanogen halide such as cyan bromide to react with an amino group of a ligand; a method of tosylating or tresylating a hydroxyl group of a support, and subjecting the support to react with an amino group of a ligand; a method of introducing an epoxy group to a support by means of, for example, bisepoxide, epichlorohydrin, and subjecting the support to react with an amino group, a hydroxyl group or a thiol group of a ligand; and a method of using a support having an epoxy group, and subjecting the support to react with an amino group, a hydroxyl group or a thiol group of a ligand.

The alcoholic hydroxyl group, which is a ring-opened epoxy group produced when an epoxy group is ring-opened, plays roles of hydrophilizing the support surface, preventing non-specific adsorption of, for example, proteins, and also enhancing toughness of the support in water to thereby prevent destruction of the support at a high flow rate. Therefore, in the case where the remaining epoxy groups that are not bound to ligand exist in the support after immobilization of the ligand, the remaining epoxy groups are preferably opened. As the method for opening the epoxy ring in a support, for example, a method of stirring the support in water solvent with an acid or an alkali, under heating or at room temperature, may be used. Furthermore, epoxy groups may also be ring-opened by using a blocking agent having a mercapto group such as mercaptoethanol or thioglycerol, or a blocking agent having an amino group such as monoethanolamine. The most preferred ring-opened epoxy group is a ring-opened epoxy group obtainable by ring-opening an epoxy group contained in a support by using thioglycerol. Thioglycerol is advantageous in that, the compound has lower toxicity than, for example, mercaptoethanol as a raw material, and the epoxy ring-opened group to which the thioglycerol is added exhibits lower non-specific adsorption than a ring-opened group obtained by using a blocking agent having an amino group, and high dynamic binding capacity.

If necessary, a molecule (spacer) having an arbitrary length may be introduced between the support and the ligand. Examples of the spacer include a polymethylene chain, a polyethylene glycol chain, and saccharides.

1.2. Ligand
1.2.1. Anchor Peptide

The immunoglobulin-binding protein which is a ligand is represented by the formula (1).

$$R-R^2 \quad (1)$$

This immunoglobulin-binding protein (hereinafter, also referred to as "protein 1"), as described above, can be bound to a support by, for example, subjecting the protein to react with an epoxy group on the support.

In the formula (1) described above, R may be an anchor peptide. The anchor peptide can be used for binding a ligand molecule to a support. The anchor peptide can contain an amino acid motif having at least one neutral polar residue and at least one basic polar residue. In an embodiment, the anchor peptide can further contain at least one neutral non-polar residue. The neutral polar residue may be a threonine residue (T) and a serine residue (S), the basic polar residue may be a lysine residue (K), and the neutral non-polar residue may be an alanine residue (A).

The anchor peptide immobilizes ligand molecule $R^2$ on the support, and on the other hand, is appropriate to substantially retain the function of the ligand molecule. That is, while the ligand molecule is immobilized on the support, the anchor peptide can retain at least about 50% of the function of the ligand molecule, for example, the immunoglobulin binding. In an embodiment of the present invention, the anchor peptide described above (or may be referred to as linker) can contain a motif having at least two amino acid residues. The amino acid motif of the anchor peptide can equivalently contain the three groups of neutral non-polar residue, neutral polar residue, and basic polar residue. Anchor sequence can also contain only the neutral polar residue and basic non-polar residue in various combinations or arrangements.

In the formula (1), the number of amino acid residues contained in the amino acid sequence of polypeptide represented by R is preferably 4 to 30, and more preferably 4 to 20. The amino acid sequence of R contains an amino acid sequence represented by at least ATK or ASK. The amino acid sequence represented by ATK or ASK may be contained in plural, and the amino acid sequence represented by the combination of ATK and ASK for example, ATKASK (SEQ ID NO: 44) or ASKATK (SEQ ID NO: 45), may be contained.

In an embodiment, the R may contain a polypeptide represented by an amino acid sequence represented by formula XX-UU-XX (SEQ ID NO: 48)(provided that each X may be K, S, or T; and U may be an optional amino acid), or an amino acid sequence represented by formula XXX-GA-XX (SEQ ID NO: 49)(provided that each X may be A, K, S, or T).

The polypeptide may be an amino acid sequence ATKASK, or the derivative thereof that has at least 50% identity to and is functionally equivalent to the amino acid sequence.

Alternatively, the polypeptide may be an amino acid sequence ATKGATK, or the derivative thereof that has at least 50% identity to and is functionally equivalent to the amino acid sequence.

Furthermore, the amino acid sequence of R may also contain a TEV recognition sequence. The "TEV recognition sequence" in the present invention refers to an amino acid sequence that can be recognized as a specific cleavage site by a TEV (Tobacco Etch Virus) protease, however, it is not absolutely necessary that the TEV recognition sequence can be actually cleavable by a TEV protease. Examples of the "TEV recognition sequence" include the amino acid sequence ENLYFQG (for example, the 10th to 16th amino acid residues of SEQ ID NO: 22), and an amino acid sequence having 70% or more identity to the amino acid sequence, preferably 80% or more, and more preferably 90% or more, and recognized by a TEV protease (not absolutely necessary to be cleaved by the TEV protease).

The anchor peptide may be provided as a fusion product containing the anchor peptide and a ligand molecule. The anchor peptide may be N- or C-terminus extension of a ligand protein.

The anchor peptide, or a fusion product containing the anchor peptide and a ligand protein may be synthesized by any method known in the field of peptide synthesis. Examples of the method include solid phase synthesis (Merrifield (1964) J. Am. Chem. Assoc. 65:2149; J. Am. Chem. Soc. 85:2149, 1963; and Int. J. Peptide Protein Res. 35:161-214, 1990), and peptide synthesis in a homogenous solution (Methods of Organic Chemistry, E. Wansch (Ed.) Vol. 15, pts. I and II, Thieme, Stuttgart, 1987).

Alternatively, the anchor peptide, or a fusion product containing the anchor peptide and a ligand protein may be synthesized by a recombinant method known in the field. In this case, the anchor peptide may be usually bound to or fused with a terminus of a ligand protein so that the function of the protein may be substantially retained. Therefore, by the ligand protein, the anchor may be bound to the N-terminus or C-terminus. In a certain case, the anchor peptide may be bound to both termini, or may be bound to an amino acid residue other than the terminal residues.

The ligand molecule is bound to or fused with the anchor peptide of the present invention, and then the fusion product can be immobilized on the support. Alternatively, the anchor peptide may be bound to a support by a chemical procedure, a recombinant method, or using an enzyme, before binding to the protein ligand. An appropriate support is as described in 1.1.1.

The anchor peptide may be labeled to increase the statistical power in assay as understood by an ordinary person skilled in the art. Labeling is not limited, however, examples of the labeling include radioactive labeling, fluorescent labeling, and cytotoxic labeling. The anchor peptide may be provided together with a carier protein, for example, by binding to bovine serum albumin (BSA) or keyhole limpet hemocyanin. The anchor peptide may also have biotin-GGYG sequence at the N-terminus. According to the sequence, peptide concentration measurement by OD280 of tyrosine (Y) may be performed. Biotin moiety at the N-terminus may be a ligand of ELISA assay using avidin-HRP.

1.2.2. Immunoglobulin-Binding Protein

In the formula (1) described above, $R^2$ represents a polypeptide consisting of 50 to 500 amino acid residues that contains an immunoglobulin-binding domain consisting of an amino acid sequence represented by SEQ ID NO: 1 or SEQ ID NO: 2, the partial sequence thereof, or an amino acid sequence having 70% or more identity to these sequences.

For example, as $R^2$, a polypeptide containing at least one immunoglobulin-binding domain consisting of an amino acid sequence represented by SEQ ID NO: 1 or SEQ ID NO: 2, the partial sequence thereof, or an amino acid sequence having 70% or more identity to these sequences is mentioned. Preferably 2 to 12 immunoglobulin-binding domains are contained, and more preferably 3 to 8 immunoglobulin-binding domains are contained.

The amino acid sequence represented by SEQ ID NO: 1 represents an amino acid sequence of C domain that is an immunoglobulin-binding domain of protein A derived from *Staphylococcus aureus*.

Therefore, the amino acid sequence represented by SEQ ID NO: 2 represents an amino acid sequence of a variant in which Gly at the 29th amino acid residue in the amino acid sequence of the C domain is substituted with Ala (C domain G29A variant). This C domain G29A variant has a binding ability to immunoglobulin, and has improved alkali resistance as compared with the parent C domain represented by SEQ ID NO: 1.

Further, the partial sequence of the amino acid sequence represented by SEQ ID NO: 1 is a fragment of C domain (C fragment) having at least a fragment of the amino acid sequence of the C domain, and for example, a fragment having 90% or more of the amino acid sequence of the C domain is preferred, while a fragment having 95% or more is more preferred. A polypeptide consisting of the partial sequence has a binding ability to immunoglobulin.

Further, the partial sequence of the amino acid sequence represented by SEQ ID NO: 2 is a fragment of C domain G29A variant (CG29A fragment) having at least a fragment of the amino acid sequence of the C domain G29A variant, and for example, a fragment having 90% or more of the amino acid sequence of the C domain G29A variant is preferred, while a fragment having 95% or more is more preferred. A polypeptide consisting of the partial sequence has a binding ability to immunoglobulin.

Further, an amino acid sequence having 70% or more identity to the amino acid sequence represented by SEQ ID NO: 1 is a variant of the C domain, and for example, has 70% or more identity to the amino acid sequence of C domain, preferably 80% or more, more preferably 90% or more, furthermore preferably 95% or more, and still preferably 98% or more.

The variant of C domain has a binding ability to immunoglobulin, and preferably has improved alkali resistance as compared with the C domain represented by SEQ ID NO: 1. In this case, whether the variant of the C domain has improved alkali resistance as compared with the C domain represented by SEQ ID NO: 1 or not, may be confirmed by the method described in Examples (3. Test Example) presented below.

Further, an amino acid sequence having 70% or more identity to the amino acid sequence represented by SEQ ID NO: 2 is a variant of the C domain G29A variant, and for example, has 70% or more identity to the amino acid sequence of C domain G29A variant, preferably 80% or more, more preferably 90% or more, furthermore preferably 95% or more, and still preferably 98% or more; and has Ala at a position corresponding to the 29th position of C domain amino acid sequence (SEQ ID NO: 1).

The variant of the C domain G29A variant has a binding ability to immunoglobulin, and preferably has improved alkali resistance as compared with the C domain G29A variant. In this case, whether the variant of the C domain G29A variant has improved alkali resistance as compared with the C domain G29A variant or not, may be confirmed by the method described in Examples (3. Test Example) presented below.

Further, an amino acid sequence having 70% or more identity to the partial sequence is a variant of the C fragment or the CG29A fragment, and for example, has 70% or more identity to the amino acid sequence of C fragment or CG29A fragment, preferably 80% or more, more preferably 90% or more, furthermore preferably 95% or more, and still preferably 98% or more.

The variant of the C fragment or CG29A fragment has a binding ability to immunoglobulin, and preferably has improved alkali resistance as compared with the fragment. In this case, whether a variant of the fragment has improved alkali resistance as compared with the parent fragment, may be confirmed by the method described in Examples (3. Test Example) presented below.

The immunoglobulin-binding domain consisting of an amino acid sequence represented by SEQ ID NO: 1 or SEQ ID NO: 2, the partial sequence thereof, or an amino acid sequence having 70% or more identity to these sequences preferably has Val at a position corresponding to the 1st position of C domain amino acid sequence (SEQ ID NO: 1). As an example of such immunoglobulin-binding domain, a domain consisting of the amino acid sequence represented by SEQ ID NO: 3 may be mentioned.

Further, "a position corresponding to" a certain position on the amino acid sequence of the present specification may be determined by sequence comparison with sequence alignment based on a known algorithm.

The variant may be produced in accordance with a known procedure such as, for example, a site-specific mutation by modifying an immunoglobulin-binding protein such as C domain of natural protein A with the addition, deletion or substitution of amino acid residues, chemical modification of amino acid residues.

R² can further contain immunoglobulin-binding domains other than the described above. Examples of the immunoglobulin-binding domains other than the described above include, for example, A, B, D, and E domains of natural protein A, and the variant thereof.

In R², as to the binding between each immunoglobulin-binding domain, C-terminus of one domain may be directory bound to N-terminus of another domain, or may also be bound via a peptide having 1 to 10 amino acid residues. As the peptide, for example, a peptide represented by EF is preferably mentioned.

The terminus at which R² binds to R may be C-terminus or N-terminus of the immunoglobulin-binding domain contained in R².

The total number of amino acid residues constituting the protein 1 is preferably 70 to 1,000, and in the case where the protein 1 is used for the use of binding to support particles for affinity chromatography, the total number is more preferably 80 to 600.

1.2.2.2. Production of Protein 1

As a standard technology for producing the protein 1, for example, known gene recombination technologies that are described in Frederick M. Ausbel, et al., Current Protocols in Molecular Biology; and Sambrook, et al., ed., Molecular Cloning (Cold Spring Harbor Laboratory Press, 3$^{rd}$ edition, 2001), may be utilized. Specifically, an expression vector containing a nucleic acid sequence encoding a desired modified protein (protein 1) is used for transformation of a host such as E. coli, and the cell is cultured in an appropriate liquid medium, to obtain the protein 1 in a large amount and economically from the cells after culturing. As a preferred expression vector, any one of known vectors being capable of reproduction in bacteria may be used, and examples thereof include the plasmids described in U.S. Pat. No. 5,151,350, and the plasmids described in Sambrook, et al., ed., Molecular Cloning (Cold Spring Harbor Laboratory Press, 3$^{rd}$ edition, 2001). Furthermore, as a host, the host is not particularly limited, and a known host used for expression of recombinant protein including bacteria such as *E. coli*, fungi, insect cells, mammalian cells may be used. Any method that is known in the art, for example, a known method described in Sambrook, et al., ed., Molecular Cloning (Cold Spring Harbor Laboratory Press, 3$^{rd}$ edition, 2001), may be used depending on each host for transformation of the host by introducing a nucleic acid therein. The method of culturing the transformed bacteria and collecting an expressed protein is well known to ordinary person skilled in the art, and is also illustrated in the Examples of the present invention. Further, while the procedure described above, a methionine residue at the N-terminus of the protein may be cleaved by methionine aminopeptidase (The Proteomics of N-terminal Methionine Cleavage, Molecular & Cellular Proteomics 5.12, p 2336-2349, 2006). Such a protein may be also used as an immunoglobulin-binding protein of the present invention. For example, in the present invention, the protein of the sequence in which a methionine residue at the N-terminus of SEQ ID NO: 22 is cleaved may be used as an immunoglobulin-binding protein that is the same as that of SEQ ID NO: 22, and the same is applied to other sequences.

The nucleic acid according to another embodiment of the present invention encodes an immunoglobulin-binding protein (protein 1) or the functional variant thereof. According to the present invention, the "functional variant" of an immunoglobulin-binding protein is an immunoglobulin-binding protein modified by, for example, partial addition, deletion or substitution of amino acid residues, chemical modification of amino acid residues, and means a variant which retains 70% or more, preferably 80% or more, more preferably 90% or more, furthermore preferably 95% or more, and still preferably 98% or more homology with the amino acid sequence of the immunoglobulin-binding protein before modification, and which may be used as a protein equivalent to the immunoglobulin-binding protein before modification in terms of the immunoglobulin-binding activity.

Furthermore, as discussed above, the protein 1 may be a protein containing one or more (preferably 2 to 12, and more preferably 3 to 8) immunoglobulin-binding domains. An appropriate expression plasmid that encodes such a protein may be produced, for example, by a known method such as described in the Examples of the present invention, and thus, a protein containing one or more immunoglobulin-binding domains can be easily produced.

1.2.2.3. Function and Effect

The support according to the present embodiment has high dynamic binding capacity (DBC) for IgG at an early stage and shows high resistance against washing under alkaline conditions (for example, washing using an alkaline liquid such as sodium hydroxide solution at 0.01 M to 0.8 M).

1.3. Method for Isolating Immunoglobulin

The method for isolating immunoglobulin according to an embodiment of the present invention is described hereafter. The method for isolating immunoglobulin according to the present embodiment includes a step of applying a sample containing immunoglobulin in the support for affinity chromatography described above to adsorb the immunoglobulin to the support (first step); and a step of eluting the immunoglobulin from the support (second step); and further preferably includes a step of washing the support with an alkaline liquid after the second step (third step).

In the first step, a sample containing immunoglobulin is applied to, for example, a column filled with the support for affinity chromatography, under the conditions where the immunoglobulin adsorbs to the ligand. In this first step, most of the substances other than immunoglobulin in the sample pass through the column without being adsorbed to the ligand. After that, if necessary, in order to remove some substances that are weakly retained by the ligand, the support may be washed with a neutral buffer solution containing a salt such as NaCl.

In the second step, the immunoglobulin adsorbed to the ligand is eluted by applying an appropriate buffer solution at pH 2 to 5. By collecting the eluent, immunoglobulin can be isolated from the sample.

In the method for isolating immunoglobulin according to the present embodiment, preferably the third step is carried out following the second step. In the third step, the support is washed with an alkaline liquid (CIP washing). Examples of the alkaline liquid used in the third step, for example, include an aqueous sodium hydroxide solution, an aqueous potassium hydroxide solution, triethylamine, and tetrabutylammonium hydroxide.

The support for affinity chromatography of the present invention stably retains the immunoglobulin binding ability due to the high alkali resistance of protein ligand even after the washing in the third step, therefore, the support can be repeatedly used for the immunoglobulin isolation method of the present invention.

EXAMPLES

2. Examples

Hereinafter, the filler for affinity chromatography according to the present embodiment is more specifically explained by way of Examples. Furthermore, the following descriptions only generally illustrate the embodiments of the present invention, and the scope of the present invention is not limited to such descriptions.

2.1. Production Example 1

Synthesis of Porous Particles 8.2 g of glycidyl methacrylate (manufactured by Mitsubishi Rayon Co., Ltd.), 65.9 g of trimethylolpropane trimethacrylate (manufactured by Sartomer Company, Inc.), and 90.6 g of glycerin monomethacrylate (manufactured by NOF Corp.) were dissolved in 245.8 g of 2-octanone (manufactured by Toyo Gosei Co., Ltd.) and 62 g of acetophenone (manufactured by Wako Pure Chemical Industries, Ltd.), and 2 g of 2,2'-azoisobutyronitrile (manufactured by Wako Pure Chemical Industries, Ltd.) was added thereto. Thus, an organic monomer solution was prepared.

Subsequently, 8.5 g of polyvinyl alcohol (PVA-217 manufactured by Kuraray Co., Ltd.), 0.43 g of sodium dodecyl sulfate (EMAL 10G manufactured by Kao Corp.), and 21.3 g of sodium sulfate (manufactured by Wako Pure Chemical Industries, Ltd.) were added to 4240 g of pure water, and the mixture was stirred overnight, to prepare an aqueous solution.

Next, the aqueous solution thus obtained was introduced into a 7-L separable flask equipped with a thermometer, a impeller and a cooling tube, and was placed in a warm water bath. Stirring was started at 600 rpm in a nitrogen atmosphere. Subsequently, the separable flask was warmed by a warm water bath, and when the temperature of the aqueous solution reached 85° C., the organic monomer solution was added to this aqueous solution by using a dropping funnel. The mixture was stirred for 5 hours.

Subsequently, the reaction liquid was cooled, and then transferred into a 5-L bottle made of polypropylene. The reaction liquid was left to stand until the particles floated, and excess water was discarded by suctioning the lower layer. Furthermore, acetone was added to this reaction liquid, and thereby particles were settled. Subsequently, the reaction liquid was left to stand for 3 minutes, and acetone was removed by decantation. This operation was repeated twice, and then particles were settled by adding water. Furthermore, the reaction liquid was left to stand for 3 minutes, and decantation was performed. This operation was repeated twice, and thereby the particles were washed. Furthermore, a dispersion liquid of the particles was replaced with acetone again, and the particles were air dried overnight and then dried in a vacuum dryer. Thus, 90 g of porous particles (hereinafter, indicated as PB) were obtained. The average particle size of PB was 43 μm, and the specific surface area was 83 m$^2$/g.

2.2. Production Example 2

Production of Recombinant Immunoglobulin-Binding Protein (JX01)

In the present Production Example and the following Production Example, PCR Purification Kit of GE Healthcare was used for the purification of DNA. The restriction enzyme was purchased from New England Biolabs. The enzyme for PCR was purchased from Fermentas. The primer for PCR was purchased from Sigma. Ligation was carried out by T4 DNA ligase (Invitrogen). DH5alpha cell was purchased from Invitrogen. BL21 cell was purchased from STRATAGENE. pET24a-d(+) was purchased from Novagen. Unless otherwise described, all the experiments were carried out under the recommendation conditions of the supplier.

2.2.1. Construction of JX01 Plasmid (JX01-pETM11)

Plasmid JX01-pETM11 containing a DNA (SEQ ID NO: 3) encoding C*domain that is an A1V/G29A variant of C domain of protein A was constructed by the following procedure.

(1) Construction of SP1B*-pETM11

By using a DNA sequence of protein A (cDNA of *Staphylococcus aureus* (ATCC, 10832)) as a template, and using the following primer 1 (SEQ ID NO: 4) and primer 2 (SEQ ID NO: 5), PCR was carried out, the DNA thus obtained was introduced into pETM11, and thus plasmid SP1B*-pETM11 encoding B*domain (an A1V variant of B domain) was constructed. In SP1B*-pETM11, a TEV recognition sequence is added at the N-terminus side, and a base sequence SP1B*sequence (SEQ ID NO: 6) encoding the B*domain that is surrounded by the NcoI site and SacI site, was contained.

TABLE 1

```
Primer 1           5'
(with Nco I site): GGCCATGGTTGTGGATAACAAATTC 3' (SEQ ID NO: 4)

Primer 2           5'
(with Sac I site): GGAGCTCCTATTTTTTGGAGCTTG 3' (SEQ ID NO: 5)
```

PCR conditions are as follows: Step 1: at 94° C. for 1 minute (1 cycle), Step 2: at 94° C. for 30 seconds→at 55° C. for 30 seconds→at 72° C. for 2.5 minutes (25 cycles), and Step 3: at 72° C. for 10 minutes (1 cycle), and then held at 4° C.

A PCR product was purified with a PCR purification kit (GE Healthcare), and electrophoresis was carried out at 100° C. for 45 minutes by using a 1% agarose TAE gel.

(2) Construction of SP1B**-pETM11

A plasmid encoding A1V/G29A of B domain was constructed from SP1B*-pETM11 by PCR-assisted mutagenesis. Particularly, the DNA obtained from SP1B*-pETM11 via the multistep PCR-assisted mutagenesis was introduced into pETM11, and SP1B-pETM11 containing a base sequence SP1B (SEQ ID NO: 7) was constructed.

The following primer was used for the PCR-assisted mutagenesis.

TABLE 2

The first step: a primer for G29A variation

Forward: 5' GCGAAGAACAACGCAATGCTTTCATCCAAAGCCTAAAAG 3' (SEQ ID NO: 8)

Reverse: 5' CTTTTAGGCTTTGGATGAAAGCATTGCGTTGTTCTTCGC 3' (SEQ ID NO: 9)

The second step: addition of ATK

Forward: CTTTATTTTCAGGGCGCCACCAAAGTGGATCATAAATTCAAC (SEQ ID NO: 10)

Reverse: GTTGAATTTATGATCCACTTTGGTGGCGCCCTGAAAATAAAG (SEQ ID NO: 11)

The third step: addition of ASK

Forward: GGCGCCACCAAAGCTAGCAAAGTGGATCATAAATTC (SEQ ID NO: 12)

Reverse: GAATTTATGATCCACTTTGCTAGCTTTGGTGGCGCC (SEQ ID NO: 13)

PCR conditions are as follows: Step 1: at 94° C. for 1 minute (1 cycle), Step 2: at 94° C. for 30 seconds→at 55° C. for 1 minute→at 68° C. for 15 minutes (18 cycles), and Step 3: at 68° C. for 15 minutes (1 cycle), and held at 4° C.

(3) Construction of SP1C*-pETM11

A plasmid of C*domain that is a variant of A1V/G29A of SP1Bdomain was constructed by PCR-assisted mutagenesis. Particularly, the DNA obtained from SP1B-pETM11 via the multistep PCR-assisted mutagenesis was introduced into pETM11, and a plasmid SP1C*-pETM11 containing a base sequence SP1C* (SEQ ID NO: 14) encoding C*domain was constructed.

The following primer was used for the PCR-assisted mutagenesis.

TABLE 3

| The first step: a primer for N23T1 variation | |
| --- | --- |
| Forward: 5' ACATTTACCTACCTTAAGCGAAGAACAACG 3' | (SEQ ID NO: 15) |
| Reverse: 5' CGTTGTTCTTCGCTTAAGGTAGGTAAATGT 3' | (SEQ ID NO: 16) |
| The second step: a primer for Q40V and A42K | |
| Forward: GCCTAAAAGATGACCCAAGCGTGAGCAAAAACCTTTTAGCAGAAGC | (SEQ ID NO: 17) |
| Reverse: GCTTCTGCTAAAAGGTTTTTGCTCACGCTTGGGTCATCTTTTAGGC | (SEQ ID NO: 18) |
| The third step: a primer for N43E and L44I | |
| Forward: GACCCAAGCGTGAGCAAAGAAATCTTAGCAGAAGCTAAAAAG | (SEQ ID NO: 19) |
| Reverse: CTTTTTAGCTTCTGCTAAGATTTCTTTGCTCACGCTTGGGTC | (SEQ ID NO: 20) |

PCR conditions are as follows: Step 1: at 94° C. for 1 minute (1 cycle), Step 2: at 94° C. for 30 seconds→at 55° C. for 1 minute→at 68° C. for 15 minutes (18 cycles), and Step 3: at 68° C. for 15 minutes (1 cycle), and then held at 4° C.

(3) Construction of JX01-pETM11

By using SP1C*-pETM11 as a template, and using the following three pairs of primers respectively, PCR was carried out, and thus three base sequences encoding C*domain having each restriction enzyme site of EcoRI-EcoRI, EcoRI-SacI, and SacI-XhoI were constructed. These three base sequences were digested with a restriction enzyme corresponding to each of the three base sequences, and then the resultants were simultaneously introduced into SP1C*-pETM11 by the ligation reaction to construct a plasmid JX01-pETM11 containing base sequence of JX01 (SEQ ID NO: 21). This ligation reaction used the restriction enzyme sites of EcoRI and XhoI of SP1C*-pETM11.

TABLE 4

| A primer for JX01-pETM11 construction | |
| --- | --- |
| Construction of a domain having EcoRI-EcoRI site | |
| Forward: GGAGGAGAATTCGTGGATAACA | (SEQ ID NO: 23) |
| Reverse: GTTGTTGAATTCTTTTGGAGCT | (SEQ ID NO: 24) |
| Construction of a domain having EcoRI-SacI site | |
| Forward: GTTGTTGAATTCGTGGATAACA | (SEQ ID NO: 25) |
| Reverse: GTTGTTGAGCTCTTTTGGAGCTTGTGCATCATTTAG | (SEQ ID NO: 26) |

TABLE 4-continued A primer for JX01-pETM11 construction Construction of a domain having SacI-XhoI(+stop) site Forward: GGAGGAGAGCTCGTGGATAACAAA    (SEQ ID NO: 27)

Reverse: GTTGTTCTCGAGCTATTTTGGAGCTTGTGCATCATT    (SEQ ID NO: 28)

PCR conditions are as follows: Step 1: at 94° C. for 1 minute (1 cycle), Step 2: at 94° C. for 30 seconds→at 55° C. for 30 seconds→at 68° C. for 1.5 minutes (18 cycles), and Step 3: at 68° C. for 10 minutes (1 cycle), and then held at 4° C.

In order to amplify DNA, the JX01-pETM11 obtained by ligation reaction was introduced into DH5alpha competent cell for transformation. A positive colony was selected, and it was confirmed by DNA sequencing that a regular sequence was inserted. After that, JX01-pETM11 having a regular DNA sequence was introduced into BL21 cell for transformation.

2.2.2. Expression and purification of JX01

The JX01-pETM11 vector thus obtained was introduced into E. coli (strain BL21) cell (manufactured by Stratagene Corp.) and cultured, 1 mM IPTG; manufactured by Sigma-Aldrich Company) was added thereto at 18° C., and the cells were incubated for 15 hours. Thus, a recombinant immunoglobulin-binding protein was expressed. Prior to induction, the cells were incubated at 37° C. until the absorbance (OD600) reached about 0.6. After the protein was expressed, the cells were harvested and homogenized in a Tris buffer solution at pH 8.0.

The recombinant immunoglobulin-binding protein thus obtained was purified by Ni affinity chromatography (Ni-NTA (nitrilotriacetic acid) particles, manufactured by Qiagen N.V.). The purified immunoglobulin-binding protein was further purified by anion exchange chromatography (Q-Sepharose FF, manufactured by GE Healthcare Bioscience Corp.). The purity of the immunoglobulin-binding protein confirmed by SDS-PAGE was 96%. The immunoglobulin-binding protein thus purified was termed as JX01 (SEQ ID NO: 22).

2.3. Production Example 3

Production of Recombinant Immunoglobulin-Binding Protein (JX02)

To 15 mL of a buffer (pH 8.0) of 50 mM Tris-hydrochloric acid, 0.5 mM EDTA and 1 mM DTT, 150 mg of JX01 and 900 U of MobiTEV protease (MoBiTec GmbH) were added, and the mixture was stirred at 30° C. for 12 hours. Thus, the TEV recognition sequence of JX01 was cleaved. The JX01 cleaved with TEV protease was passed through a Ni-NTA column (volume: 4 mL), and thus crude JX02, in which the His-tagged site of JX01 was cleaved, was collected. The crude JX02 thus obtained was further purified by anion exchange chromatography (Q-Sepharose FF, manufactured by GE Healthcare Bioscience Corp.) in a HEPES buffer solution at pH 7.5. This JX02 was concentrated with a centrifugal concentrator (Vivaspin 20, manufactured by Sartorius AG), and then the protein was dialyzed for 12 hours in 10 mM HEPES buffer (pH 7.5). Thus, JX02 (SEQ ID NO: 29) was prepared.

2.4. Production Example 4

Production of Recombinant Immunoglobulin-Binding Protein (JX03)

2.4.1. Construction of JX03-pET24-a-d(+)

By using a JX01-pETM11 as a template, and using the following primer 3 (SEQ ID NO: 30) and primer 4 (SEQ ID NO: 31), PCR was carried out, and thus the DNA encoding polypeptide 4XC* having ATKASK at the N-terminus of JX01 was constructed. This DNA was introduced into pET24-a-d(+), and a JX03-pET24-a-d(+) plasmid was constructed. NdeI and XhoI sites of pET24-a-d(+) were used for the introduction. The ligation reaction was carried out by using T4 DNA ligase. In order to amplify DNA, the JX03-pET24-a-d(+) obtained by ligation reaction was introduced into DH5alpha competent cell for transformation. A positive colony was selected and cultured, and it was confirmed by DNA sequencing that a regular sequence was inserted. After that, JX03-pET24-a-d(+) having a regular JX03 base sequence (SEQ ID NO: 32) was introduced into BL21 cell for transformation.

TABLE 5

| Primer 3 (with NdeI site): | 5' GAAGAACATATGGCCACCAAAGC 3' | (SEQ ID NO: 30) |
| Primer 4 (with XhoI site): | 5' GGTGGTCTCGAGCTATT 3' | (SEQ ID NO: 31) |

PCR conditions are as follows: Step 1: at 94° C. for 1 minute (1 cycle), Step 2: at 94° C. for 30 seconds→at 55° C. for 30 seconds→at 68° C. for 2.5 minutes (25 cycles), and Step 3: at 68° C. for 10 minutes (1 cycle), and then held at 4° C.

2.4.2. Expression and Purification of JX03

The JX03-pET24-a-d(+) thus obtained was introduced into E. coli (strain BL21) cell and cultured, 1 mM IPTG (manufactured by Sigma-Aldrich Company) was added thereto at 18° C., and the cells were incubated for 15 hours. Thus, a recombinant immunoglobulin-binding protein was expressed. Prior to induction, the cells were incubated at 37° C. until the absorbance (OD600) reached about 0.6. After the protein was expressed, the cells were harvested and homogenized in a Tris buffer solution at pH 8.0.

The recombinant immunoglobulin-binding protein thus obtained was purified by anion exchange chromatography (Q-Sepharose FF, manufactured by GE Healthcare Bioscience Corp.) and cation exchange chromatography (SP-Sepharose FF, manufactured by GE Healthcare Bioscience Corp.). The purity of the immunoglobulin-binding protein confirmed by SDS-PAGE was 96% or more. The immunoglobulin-binding protein thus purified was termed as JX03 (SEQ ID NO: 33).

2:5. Production Example 5

Production of Recombinant Immunoglobulin-Binding Protein (JX04)

2.5.1. Construction of JX04-pET24-a-d(+)

From JX03-pET24-a-d(+), via the following 2 steps, plasmid JX04-pET24-a-d(+) containing a DNA (SEQ ID NO: 34) encoding polypeptide JX04 in which N-terminus ATKASK (SEQ ID NO: 44) of JX03 was deleted and ATKASK (SEQ ID NO: 44) was added at the C-terminus was constructed.

(1) A DNA sequence encoding N-terminus ATKASK (SEQ ID NO: 44) was deleted from JX03-pET24-a-d(+) by PCR-assisted mutagenesis using the following primer.

TABLE 6

| A primer for deletion of N-terminus ATKASK (SEQ ID NO: 44) |
|---|
| Forward: GGAGATATACATATGGTAGACAACAAATTCAAC (SEQ ID NO: 36) |
| Reverse: GTTGAATTTGTTGTCTACCATATGTATATCTCC (SEQ ID NO: 37) |

PCR conditions are as follows: Step 1: at 94° C. for 1 minute (1 cycle), Step 2: at 94° C. for 30 seconds→at 55° C. for 1 minute→at 68° C. for 15 minutes (18 cycles), and Step 3: at 68° C. for 15 minutes (1 cycle), and then held at 4° C.

The plasmid thus obtained was introduced into DH5alpha competent cell and the positive colony was cultured, plasmid DNA was purified, and it was confirmed by DNA sequencing that a DNA sequence of N-terminus ATKASK (SEQ ID NO: 44) was deleted.

(2) C-terminus ATKASK (SEQ ID NO: 44) sequence was added to a plasmid obtained in (1) in which the N-terminus ATKASK (SEQ ID NO: 44) sequence was deleted, by PCR-assisted mutagenesis using the following primer.

TABLE 7

| A primer for addition of C-terminus ATKASK (SEQ ID NO: 44) |
|---|
| Forward: CACAAGCTCCAAAAGCCACCAAAGCTAGCAAATAGCTCGAGCACC (SEQ ID NO: 38) |
| Reverse: GGTGCTCGAGCTATTTGCTAGCTTTGGTGGCTTTTGGAGCTTGTG (SEQ ID NO: 39) |

PCR conditions are as follows: Step 1: at 94° C. for 1 minute (1 cycle), Step 2: at 94° C. for 30 seconds→at 55° C. for 1 minute→at 68° C. for 15 minutes (18 cycles), and Step 3: at 68° C. for 15 minutes (1 cycle), and then held at 4° C.

The plasmid thus obtained was introduced into DH5alpha competent cell and the cell was cultured, plasmid DNA was purified, and it was confirmed by DNA sequencing that a DNA sequence of C-terminus ATKASK was added. The plasmid JX04-pET24-a-d(+) having a regular DNA sequence was introduced into BL21 cell for transformation.

2.5.2. Expression and Purification of JX04

The JX04-pET24-a-d(+) thus obtained was introduced into E. coli (strain BL21) cell and cultured, 1 mM IPTG (manufactured by Sigma-Aldrich Company) was added thereto at 18° C., and the cells were incubated for 15 hours. Thus, a recombinant immunoglobulin-binding protein was expressed. Prior to induction, the cells were incubated at 37° C. until the absorbance (OD600) reached about 0.6. After the protein was expressed, the cells were harvested and homogenized in a Tris buffer solution at pH 8.0.

The recombinant immunoglobulin-binding protein thus obtained was purified by anion exchange chromatography (Q-Sepharose FF, manufactured by GE Healthcare Bioscience Corp.) and cation exchange chromatography (SP-Sepharose FF, manufactured by GE Healthcare Bioscience Corp.). The purity of the immunoglobulin-binding protein confirmed by SDS-PAGE was 96% or more. The immunoglobulin-binding protein thus purified was termed as JX04 (SEQ ID NO: 35).

2.6. Production Example 6

Production of Recombinant Immunoglobulin-Binding Protein (JX05)

2.6.1. Construction of JX05-pET24-a-d(+)

From JX03-pET24-a-d(+), via the three steps shown in the following FIG. 1, plasmid JX05-pET24-a-d(+) containing a DNA sequence (SEQ ID NO: 40) encoding polypeptide JX05 in which eight immunoglobulin-binding domains and N-terminus ATKASK (SEQ ID NO: 44) were contained was constructed.

(1) JX03-pET24-a-d(+) was digested by AccI restriction enzyme.

(2) 4-Domain plasmid pUC57/4C having two AccI sites (pUC57 was purchased from GenScript) was constructed by PCR-assisted mutagenesis using the following primer.

TABLE 8

| Forward: CACAAGCACCGAAAGTAGACCTCATCGGATCCC (SEQ ID NO: 42) |
|---|
| Reverse: GGGATCCGATGAGGTCTACTTTCGGTGCTTGTG (SEQ ID NO: 43) |

PCR conditions are as follows: Step 1: at 94° C. for 1 minute (1 cycle), Step 2: at 94° C. for 30 seconds→at 55° C. for 1 minute→at 68° C. for 15 minutes (18 cycles), and Step 3: at 68° C. for 15 minutes (1 cycle), and then held at 4° C.

The plasmid thus obtained was introduced into DH5alpha competent cell and the positive colony was cultured, plasmid DNA was purified, and it was confirmed by DNA sequencing that the second AccI site was added. This plasmid was also digested by AccI restriction enzyme.

(3) Ligation of JX03-pET24-a-d(+) digested by AccI restriction enzyme and pUC57/4C was carried out by using T4 DNA Ligase to construct JX05-pET24-a-d(+). In order to amplify DNA, the new JX05-pET24-a-d(+) obtained by ligation reaction was introduced into DH5alpha competent cell for transformation. A positive colony was selected, and it was confirmed by DNA sequencing to be a regular sequence. After that, JX05-pET24-a-d(+) having a regular DNA sequence was introduced into BL21 cell for transformation.

2.6.2. Expression and Purification of JX05

The JX05-pET24-a-d(+) thus obtained was introduced into E. coli (strain BL21) cell and cultured, 1 mM IPTG (manufactured by Sigma-Aldrich Company) was added thereto at 18° C., and the cells were incubated for 15 hours. Thus, a recombinant immunoglobulin-binding protein was expressed. Prior to induction, the cells were incubated at 37° C. until the absorbance (OD600) reached about 0.6. After the protein was expressed, the cells were harvested and homogenized in a Tris buffer solution at pH 8.0.

The recombinant immunoglobulin-binding protein thus obtained was purified by anion exchange chromatography (Q-Sepharose FF, manufactured by GE Healthcare Bioscience Corp.) and cation exchange chromatography (SP-Sepharose FF, manufactured by GE Healthcare Bioscience Corp.). The purity of the immunoglobulin-binding protein confirmed by SDS-PAGE was 96% or more. The immunoglobulin-binding protein thus purified was termed as JX05 (SEQ ID NO: 41).

2.7. Production Example 7

Immobilization of Immunoglobulin-Binding Protein on Particles-1

A liquid mixture in which 1.1 mL of PB prepared in Production Example 1, and 10 mL of a 0.1 M phosphate buffer (pH 6.8) in which 20 mg of JX02 was dispersed was prepared, and then 2.1 g of sodium sulfate was added thereto. The mixture was mixed by inverting at 25° C. for 24 hours, for binding the JX02 to PB. The particles thus produced were filtered, and then were mixed with 10 mL of 5 M thioglycerol. The mixture was subjected to react at 30° C. for 4 hours, and remaining epoxy groups were blocked. The particles were washed with PBS/0.05% Tween 20, and then washed with PBS. Thus, 1.1 mL of JX02-bound porous particles (JX02-PB1) was obtained.

According to a similar procedure as described above, porous particles (JX03-PB1, JX04-PB1, or JX05-PB1) in which any one of JX03 to JX05 was bound were obtained.

2.8. Production Example 8

Immobilization of Immunoglobulin-Binding Protein on Particles-2

A liquid mixture of 4 mL of PB prepared in Production Example 1 and 40 mL of a 0.1 M borate buffer (pH 8.0) in which 75 mg of JX02 was dispersed and 4 g of sodium sulfate was dissolved was prepared. The mixture was mixed by inverting at 25° C. for 5 hours, for binding the JX02 to PB. The particles thus produced were filtered, and then were mixed with 40 mL of 1 M thioglycerol. The mixture was subjected to react at 25° C. for 4 hours, and remaining epoxy groups were blocked. The particles were washed with 0.5 M NaOH, and then washed with 0.1 M sodium citrate buffer (pH 3.2) and 0.1 M sodium phosphate buffer (pH 7.6). Thus, 4 mL of JX02-bound porous particles (JX02-PB2) was obtained.

According to a similar procedure as described above, porous particles (JX03-PB2, JX04-PB2, or JX05-PB2) in which any one of JX03 to JX05 was bound were obtained.

3. Test Example 3.1. Measurement Example 1

Measurement of Dynamic Binding Capacity for Immunoglobulin G (IgG)

JX02-PB2 was filled in a column having an inner diameter of 0.5 cm up to a bed height of 20 cm. The column was equilibrated with a 20 mM phosphate buffer (pH 7.4), and then a 20 mM phosphate buffer containing human polyclonal IgG (5 mg/mL) was applied at a linear flow rate of 300 cm/hour. From the amount of human polyclonal IgG adsorption obtained when the human polyclonal IgG concentration in the eluent underwent 10% breakthrough by absorbance monitoring, and support volume, the dynamic binding capacity (DBC) was determined. The result of DBC was 45 mg/mL.

According to a similar procedure as described above, each DBC of JX03-PB2, JX04-PB2, and JX05-PB2 was determined.

3.2. Measurement Example 2

Measurement of Alkali Resistance

A column filled with the support used in Measurement Example 1 was mounted in AKTAprime plus, and 20 mL of 0.5 M sodium hydroxide was applied to the column. The column was removed from the apparatus and sealed, and the column was left to stand for a while (15, 30, and 45 hours) at room temperature. Subsequently, the binding capacity for human polyclonal IgG at a linear flow rate of 300 cm/hour was measured in the same manner as in Measurement Example 1. The binding capacity retention rate was determined relative to the case where the binding amount of human polyclonal IgG before the treatment with 0.5 M sodium hydroxide (Measurement Example 1) was defined as 100%.

3.4. Measurement Example 3

4 mL of Mabselect SuRe (manufactured by GE Healthcare Bioscience Corp.) was filled into a column, the DBC and binding capacity retention rate were determined in the same manner as in Measurement Examples 1 to 2.

The Measurement results are shown in Table 9. The support particles JX02-PB2 to X05-PB2 to which immunoglobulin-binding proteins (JX02 to JX05) were bound, exhibited high DBC at an early stage and a small decrease in the retention ratio of the binding capacity even if the contact time to strong alkali was increased. In each of JX02-PB1 to JX05-PB1, a similar tendency was also observed.

Accordingly, it was confirmed that the support to which a protein ligand represented by the formula (1) was immobilized, exhibited excellent alkali resistance.

TABLE 9

|  | 15 hours | | 30 hours | | 45 hours | |
|---|---|---|---|---|---|---|
| Pre DBC | DBC | Retention ratio | DBC | Retention ratio | DBC | Retention ratio |
| JX02 45 | 40 | 89.0 | 29 | 65.0 | 20 | 45.0 |
| JX03 45 | 40 | 88.7 | 29 | 64.1 | 19 | 43.1 |
| JX04 45 | 41 | 90.3 | 31 | 67.9 | 21 | 47.3 |
| JX05 46 | 45 | 96.8 | 37 | 79.8 | 26 | 57.5 |
| SuRe 40 | 35 | 87.3 | 28 | 69.0 | 18 | 44.8 |

The present invention, exemplified according to the above examples, is not intended to be limited to the embodiments described above, and various new alterations are possible. Furthermore, the present invention includes constitutions that are substantially identical with the constitutions described in the embodiments (for example, constitutions having identical functions, methods and results, or constitutions having identical purposes and results). Furthermore, the present invention includes constitutions in which the parts that are not essential in the constitutions described in the embodiments have been changed. Further, the present invention includes constitutions which provide the same operating effects, or constitutions which can achieve the same purpose, as the constitutions described in the embodiments. Further, the present invention includes constitutions to which known technologies have been added to the constitutions described in the embodiments.

The invention claimed is:

1. A support immobilizing a protein ligand comprising:
an anchor peptide consisting of 4 to 30 amino acid residues containing an amino acid sequence represented by ATK or ASK; and
an immunoglobulin binding domain consisting of the amino acid sequence that is at least 90% identical to SEQ ID NO: 1 or at least 90% identical to SEQ ID NO: 2 and that is no longer than 500 amino acid residues;
wherein the C- or N-terminus of said immunoglobulin binding domain is bound to said anchor peptide and the anchor peptide is bound to the support, optionally via a spacer; and wherein the anchor peptide comprises the sequence XX-UU-XX (SEQ ID NO:48), where X is K, S or T, and U is an optional amino acid residue which may be any amino acid residue,
wherein the anchor peptide comprises the sequence XXX-GA-XX (SEQ ID NO: 49), where X is A, K, S or T, and/or
wherein the anchor peptide comprises ASK, ASKATK (SEQ ID NO: 45), ATKASK (SEQ ID NO: 44), or ATKATK (SEQ ID NO: 47); and
wherein the support has a dynamic binding capacity for IgG that is higher than an otherwise identical support not comprising said anchor peptide after the support is treated with 0.5 M sodium hydroxide for 15 hrs.

2. The support according to claim 1, wherein the amino acid sequence having 90% or more identity to the amino acid sequence represented by SEQ ID NO: 1 or SEQ ID NO: 2 is the amino acid sequence represented by SEQ ID NO: 3.

3. The support according to claim 1, wherein the anchor peptide contains the amino acid sequence represented by a combination of ATK and ASK.

4. The support according to claim 1, wherein the anchor peptide contains the amino acid sequence represented by ATKASK (SEQ ID NO: 44) or ASKATK (SEQ ID NO: 45).

5. The support according to claim 1, wherein the anchor peptide contains the amino acid sequence represented by ASKASK (SEQ ID NO: 46).

6. The support according to claim 1, wherein the anchor peptide contains the amino acid sequence represented by ATKATK (SEQ ID NO: 47).

7. The support according to claim 1, wherein the protein ligand is immobilized on the support via epoxy group ring-opening reaction between an amino group or a thiol group in the ligand and an epoxy group in the support.

8. The support of claim 1 that is an affinity chromatography support.

9. The support of claim 8 that is in a particulate form.

10. The support of claim 8 that comprises synthetic polymer particles having a particle size ranging from 20 μm to 200 μm.

11. The support of claim 8 that comprises synthetic polymer particles having a particle size ranging from 100 nm to 400 nm.

12. The support of claim 8 that comprises porous particles having a specific surface area of 50 $m^2$/g to 150 $m^2$/g.

13. The support of claim 8 that has a dynamic binding capacity ("DBC") for human polyclonal IgG ranging from 40 to 45 after contact with 0.5 M sodium hydroxide for 15 hrs.

14. The support of claim 8 that has a retention ratio of the immunoglobulin binding domain ranging from 89.0 to 96.8 after contact with 0.5 M sodium hydroxide for 15 hrs.

15. The support of claim 8 that comprises polysaccharide particles having a particle size ranging from 50 μm to 200 μm.

16. The support of claim 8 that comprises polysaccharide particles having a particle size ranging from 500 nm to 1,400 nm.

17. The support of claim 8, wherein said protein ligand ranges in length from 70 to 1,000 amino acid residues.

18. The support of claim 8, wherein said protein ligand ranges in length from 80 to 600 amino acid residues.

19. The support of claim 1, wherein the immunoglobulin binding domain comprises G29A or an alanine substitution at a residue corresponding to G29.

20. A method for isolating an immunoglobulin comprising:
    applying a sample containing immunoglobulin through the support for affinity chromatography according to claim 1 to adsorb the immunoglobulin to the support; and
    eluting the immunoglobulin from the support.

21. A method for isolating an immunoglobulin comprising:
    applying a sample containing immunoglobulin through the support according to claim 7 to adsorb the immunoglobulin to the support; and
    eluting the adsorbed immunoglobulin from the support.

* * * * *

SEQUENCE LISTING

```
<160> NUMBER OF SEQ ID NOS: 49

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Staphylococcus aureus

<400> SEQUENCE: 2

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 3
<211> LENGTH: 58
<212> TYPE: PRT
<213> ORGANISM: Staphylococcus aureus

<400> SEQUENCE: 3

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
```

<210> SEQ ID NO 4
<211> LENGTH: 25
<212> TYPE: DNA
<213> ORGANISM: Artificial
<220> FEATURE:
<223> OTHER INFORMATION: Oligonucleotide primer

<400> SEQUENCE: 4
ggccatggtt gtggataaca aattc                                          25

<210> SEQ ID NO 5
<211> LENGTH: 25
<212> TYPE: DNA
<213> ORGANISM: Artificial
<220> FEATURE:
<223> OTHER INFORMATION: Oligonucleotide primer

<400> SEQUENCE: 5
ggagctccta tttttttgga gcttg                                          25

<210> SEQ ID NO 6
<211> LENGTH: 267
<212> TYPE: DNA
<213> ORGANISM: Staphylococcus aureus

<400> SEQUENCE: 6
atgaaacatc accatcacca tcacccatg agcgattacg acatccccac tactgagaat      60
ctttattttc agggcgccat ggttgtggat aacaaattca caaagaaca caaaatgct     120 ttctatgaaa tcttacattt acctaactta aacgaagaac aacgcaatgg tttcatccaa   180
agcctaaaag atgacccaag ccaaagcgct aaccttttag cagaagctaa aaagctaaat   240
gatgcacaag ctccaaaata ggagctc                                       267

<210> SEQ ID NO 7
<211> LENGTH: 249
<212> TYPE: DNA
<213> ORGANISM: Staphylococcus aureus

<400> SEQUENCE: 7
atgaaacacc atcaccatca ccatcacgag aatctttatt ttcagggcgc caccaaagct    60
agcaaagtgg ataacaaatt caacaaagaa caacaaaatg ctttctatga aatcttacat   120
ttacctaact aaacgaaga caacgcaat gctttcatcc aaagcctaaa agatgaccca    180
agccaaagcg ctaaccttt agcagaagct aaaaagctaa atgatgcaca agctccaaaa   240
taggagctc                                                           249

<210> SEQ ID NO 8
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 8
gcgaagaaca acgcaatgct ttcatccaaa gcctaaaag                           39

<210> SEQ ID NO 9
<211> LENGTH: 39
<212> TYPE: DNA
<213> ORGANISM: Artificial Sequence

```
<220> FEATURE:
<223> OTHER INFORMATION: Oligonucleotide primer

<400> SEQUENCE: 9
cttttaggct tggatgaaa gcattgcgtt gttcttcgc                               39

<210> SEQ ID NO 10
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 10 ctttatttc agggcgccac caaagtggat cataaattca ac                            42

<210> SEQ ID NO 11
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 11
gttgaattta tgatccactt tggtggcgcc ctgaaaataa ag                           42

<210> SEQ ID NO 12
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 12
ggcgccacca aagctagcaa agtggatcat aaattc                                 36

<210> SEQ ID NO 13
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 13
gaatttatga tccactttgc tagctttggt ggcgcc                                 36

<210> SEQ ID NO 14
<211> LENGTH: 246
<212> TYPE: DNA
<213> ORGANISM: Staphylococcus aureus

<400> SEQUENCE: 14
atgaaacacc atcaccatca ccatcacgag aatctttatt ttcagggcgc caccaaagct        60
agcaaagtgg ataacaaatt caacaaagaa caacaaaatg ctttctatga atcttacat        120 ttacctaact taaccgaaga caacgcaat gctttcatcc aaagcctaaa agatgaccca        180
agcgtgagca agaaatctt agcagaagct aaaaagctaa atgatgcaca agctccaaaa        240
gaattc                                                                  246

<210> SEQ ID NO 15
<211> LENGTH: 30
<212> TYPE: DNA
<213> ORGANISM: Artificial Sequence
<220> FEATURE:
```

```
<223> OTHER INFORMATION: Oligonucleotide primer

<400> SEQUENCE: 15
acatttacct accttaagcg aagaacaacg                                    30

<210> SEQ ID NO 16
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 16
cgttgttctt cgcttaaggt aggtaaatgt                                    30

<210> SEQ ID NO 17
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 17
gcctaaaaga tgacccaagc gtgagcaaaa accttttagc agaagc                  46

<210> SEQ ID NO 18
<211> LENGTH: 46
<212> TYPE: DNA
<213> ORGANISM: Artificial Sequence
<220> FEATURE:
<223> OTHER INFORMATION: Oligonucleotide primer

<400> SEQUENCE: 18
gcttctgcta aaggttttt gctcacgctt gggtcatctt ttaggc                   46

<210> SEQ ID NO 19
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 19
gacccaagcg tgagcaaaga aatcttagca gaagctaaaa ag                      42

<210> SEQ ID NO 20
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 20 cttttagct tctgctaaga tttctttgct cacgcttggg tc                       42

<210> SEQ ID NO 21
<211> LENGTH: 783
<212> TYPE: DNA
<213> ORGANISM: Staphylococcus aureus

<400> SEQUENCE: 21
atgaaacacc atcaccatca ccatcacgag aatctttatt ttcagggcgc caccaaagct   60
agcaaagtag acaacaaatt caacaaagaa caacaaaatg ctttctatga atcttacat   120 ttacctaact taaccgaaga acaacgcaat gctttcatcc aaagcctaaa agatgaccca  180
```

```
agcgtgagca aagaaatctt agcagaagct aaaaagctaa atgatgcaca agctccaaaa    240
gaattcgtgg ataacaaatt caacaaagaa caacaaaatg ctttctatga atcttacat    300 ttacctaact taaccgaaga acaacgcaat gctttcatcc aaagcctaaa agatgaccca    360
agcgtgagca aagaaatctt agcagaagct aaaaagctaa atgatgcaca agctccaaaa    420
gaattcgtgg ataacaaatt caacaaagaa caacaaaatg ctttctatga atcttacat    480 ttacctaact taaccgaaga acaacgcaat gctttcatcc aaagcctaaa agatgaccca    540
agcgtgagca aagaaatctt agcagaagct aaaaagctaa atgatgcaca agctccaaaa    600
gagctcgtgg ataacaaatt caacaaagaa caacaaaatg ctttctatga atcttacat    660 ttacctaact taaccgaaga acaacgcaat gctttcatcc aaagcctaaa agatgaccca    720
agcgtgagca aagaaatctt agcagaagct aaaaagctaa atgatgcaca agctccaaaa    780
tag                                                                 783
```

<210> SEQ ID NO 22
<211> LENGTH: 260
<212> TYPE: PRT
<213> ORGANISM: Artificial Sequence
<220> FEATURE:
<223> OTHER INFORMATION: Immunoglobulin binding protein JX01

<400> SEQUENCE: 22

```
Met Lys His His His His His His Glu Asn Leu Tyr Phe Gln Gly
 1               5                  10                  15

Ala Thr Lys Ala Ser Lys Val Asp Asn Lys Phe Asn Lys Glu Gln Gln
                20                  25                  30

Asn Ala Phe Tyr Glu Ile Leu His Leu Pro Asn Leu Thr Glu Glu Gln
            35                  40                  45

Arg Asn Ala Phe Ile Gln Ser Leu Lys Asp Asp Pro Ser Val Ser Lys
        50                  55                  60

Glu Ile Leu Ala Glu Ala Lys Lys Leu Asn Asp Ala Gln Ala Pro Lys
 65                  70                  75                  80

Glu Phe Val Asp Asn Lys Phe Asn Lys Glu Gln Gln Asn Ala Phe Tyr
                85                  90                  95

Glu Ile Leu His Leu Pro Asn Leu Thr Glu Glu Gln Arg Asn Ala Phe
            100                 105                 110

Ile Gln Ser Leu Lys Asp Asp Pro Ser Val Ser Lys Glu Ile Leu Ala
        115                 120                 125

Glu Ala Lys Lys Leu Asn Asp Ala Gln Ala Pro Lys Glu Phe Val Asp
    130                 135                 140

Asn Lys Phe Asn Lys Glu Gln Gln Asn Ala Phe Tyr Glu Ile Leu His
145                 150                 155                 160

Leu Pro Asn Leu Thr Glu Glu Gln Arg Asn Ala Phe Ile Gln Ser Leu
                165                 170                 175

Lys Asp Asp Pro Ser Val Ser Lys Glu Ile Leu Ala Glu Ala Lys Lys
            180                 185                 190

Leu Asn Asp Ala Gln Ala Pro Lys Glu Leu Val Asp Asn Lys Phe Asn
        195                 200                 205

Lys Glu Gln Gln Asn Ala Phe Tyr Glu Ile Leu His Leu Pro Asn Leu
    210                 215                 220

Thr Glu Glu Gln Arg Asn Ala Phe Ile Gln Ser Leu Lys Asp Asp Pro
225                 230                 235                 240

Ser Val Ser Lys Glu Ile Leu Ala Glu Ala Lys Lys Leu Asn Asp Ala
```

Gln Ala Pro Lys
        260

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 23
ggaggagaat tcgtggataa ca                                          22

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 24
gttgttgaat tcttttggag ct                                          22

<210> SEQ ID NO 25
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 25
gttgttgaat tcgtggataa ca                                          22

<210> SEQ ID NO 26
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 26
gttgttgagc tcttttggag cttgtgcatc atttag                           36

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 27
ggaggagagc tcgtggataa caaa                                        24

<210> SEQ ID NO 28
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 28
gttgttctcg agctattttg gagcttgtgc atcatt                           36

<210> SEQ ID NO 29

```
<211> LENGTH: 245
<212> TYPE: PRT
<213> ORGANISM: Artificial Sequence
<220> FEATURE:
<223> OTHER INFORMATION: Immunoglobulin binding protein JX02

<400> SEQUENCE: 29

Gly Ala Thr Lys Ala Ser Lys Val Asp Asn Lys Phe Asn Lys Glu Gln
1               5                   10                  15

Gln Asn Ala Phe Tyr Glu Ile Leu His Leu Pro Asn Leu Thr Glu Glu
            20                  25                  30

Gln Arg Asn Ala Phe Ile Gln Ser Leu Lys Asp Asp Pro Ser Val Ser
        35                  40                  45

Lys Glu Ile Leu Ala Glu Ala Lys Lys Leu Asn Asp Ala Gln Ala Pro
50                  55                  60

Lys Glu Phe Val Asp Asn Lys Phe Asn Lys Glu Gln Gln Asn Ala Phe
65                  70                  75                  80

Tyr Glu Ile Leu His Leu Pro Asn Leu Thr Glu Glu Gln Arg Asn Ala
                85                  90                  95

Phe Ile Gln Ser Leu Lys Asp Asp Pro Ser Val Ser Lys Glu Ile Leu
            100                 105                 110

Ala Glu Ala Lys Lys Leu Asn Asp Ala Gln Ala Pro Lys Glu Phe Val
        115                 120                 125

Asp Asn Lys Phe Asn Lys Glu Gln Gln Asn Ala Phe Tyr Glu Ile Leu
130                 135                 140

His Leu Pro Asn Leu Thr Glu Glu Gln Arg Asn Ala Phe Ile Gln Ser
145                 150                 155                 160

Leu Lys Asp Asp Pro Ser Val Ser Lys Glu Ile Leu Ala Glu Ala Lys
                165                 170                 175

Lys Leu Asn Asp Ala Gln Ala Pro Lys Glu Leu Val Asp Asn Lys Phe
            180                 185                 190

Asn Lys Glu Gln Gln Asn Ala Phe Tyr Glu Ile Leu His Leu Pro Asn
        195                 200                 205

Leu Thr Glu Glu Gln Arg Asn Ala Phe Ile Gln Ser Leu Lys Asp Asp
    210                 215                 220

Pro Ser Val Ser Lys Glu Ile Leu Ala Glu Ala Lys Lys Leu Asn Asp
225                 230                 235                 240

Ala Gln Ala Pro Lys
                245

<210> SEQ ID NO 30
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 30
gaagaacata tggccaccaa agc                                            23

<210> SEQ ID NO 31
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 31
ggtggtctcg agctatt                                                   17
```

<210> SEQ ID NO 32
<211> LENGTH: 747
<212> TYPE: DNA
<213> ORGANISM: Artificial Sequence
<220> FEATURE:
<223> OTHER INFORMATION: DNA encoding immunoglobulin binding protein JX03

<400> SEQUENCE: 32

```
catatggcca ccaaagctag caaagtagac aacaaattca acaagaaca acaaaatgct      60
ttctatgaaa tcttacattt acctaactta accgaagaac aacgcaatgc tttcatccaa    120
agcctaaaag atgacccaag cgtgagcaaa gaaatcttag cagaagctaa aaagctaaat    180
gatgcacaag ctccaaaaga attcgtggat aacaaattca acaagaaca acaaaatgct    240
ttctatgaaa tcttacattt acctaactta accgaagaac aacgcaatgc tttcatccaa    300
agcctaaaag atgacccaag cgtgagcaaa gaaatcttag cagaagctaa aaagctaaat    360
gatgcacaag ctccaaaaga attcgtggat aacaaattca acaagaaca acaaaatgct    420
ttctatgaaa tcttacattt acctaactta accgaagaac aacgcaatgc tttcatccaa    480
agcctaaaag atgacccaag cgtgagcaaa gaaatcttag cagaagctaa aaagctaaat    540
gatgcacaag ctccaaaaga gctcgtggat aacaaattca acaagaaca acaaaatgct    600
ttctatgaaa tcttacattt acctaactta accgaagaac aacgcaatgc tttcatccaa    660
agcctaaaag atgacccaag cgtgagcaaa gaaatcttag cagaagctaa aaagctaaat    720
gatgcacaag ctccaaaata gctcgag                                        747
```

<210> SEQ ID NO 33
<211> LENGTH: 245
<212> TYPE: PRT
<213> ORGANISM: Artificial Sequence
<220> FEATURE:
<223> OTHER INFORMATION: Immunoglobulin binding protein JX03

<400> SEQUENCE: 33

```
Met Ala Thr Lys Ala Ser Lys Val Asp Asn Lys Phe Asn Lys Glu Gln
1               5                   10                  15

Gln Asn Ala Phe Tyr Glu Ile Leu His Leu Pro Asn Leu Thr Glu Glu
            20                  25                  30

Gln Arg Asn Ala Phe Ile Gln Ser Leu Lys Asp Asp Pro Ser Val Ser
        35                  40                  45

Lys Glu Ile Leu Ala Glu Ala Lys Lys Leu Asn Asp Ala Gln Ala Pro
    50                  55                  60

Lys Glu Phe Val Asp Asn Lys Phe Asn Lys Glu Gln Gln Asn Ala Phe
65                  70                  75                  80

Tyr Glu Ile Leu His Leu Pro Asn Leu Thr Glu Glu Gln Arg Asn Ala
                85                  90                  95

Phe Ile Gln Ser Leu Lys Asp Asp Pro Ser Val Ser Lys Glu Ile Leu
            100                 105                 110

Ala Glu Ala Lys Lys Leu Asn Asp Ala Gln Ala Pro Lys Glu Phe Val
        115                 120                 125

Asp Asn Lys Phe Asn Lys Glu Gln Gln Asn Ala Phe Tyr Glu Ile Leu
    130                 135                 140

His Leu Pro Asn Leu Thr Glu Glu Gln Arg Asn Ala Phe Ile Gln Ser
145                 150                 155                 160

Leu Lys Asp Asp Pro Ser Val Ser Lys Glu Ile Leu Ala Glu Ala Lys
```

```
                165                 170                 175
Lys Leu Asn Asp Ala Gln Ala Pro Lys Glu Leu Val Asp Asn Lys Phe
            180                 185                 190

Asn Lys Glu Gln Gln Asn Ala Phe Tyr Glu Ile Leu His Leu Pro Asn
        195                 200                 205

Leu Thr Glu Glu Gln Arg Asn Ala Phe Ile Gln Ser Leu Lys Asp Asp
    210                 215                 220

Pro Ser Val Ser Lys Glu Ile Leu Ala Glu Ala Lys Lys Leu Asn Asp
225                 230                 235                 240

Ala Gln Ala Pro Lys
            245

<210> SEQ ID NO 34
<211> LENGTH: 747
<212> TYPE: DNA
<213> ORGANISM: Artificial Sequence
<220> FEATURE:
<223> OTHER INFORMATION: DNA encoding immunoglobulin binding protein
      JX04

<400> SEQUENCE: 34
catatggtag acaacaaatt caacaaagaa caacaaaatg ctttctatga aatcttacat      60
ttacctaact taaccgaaga caacgcaat  gctttcatcc aaagcctaaa agatgaccca     120
agcgtgagca agaaatctt  agcagaagct aaaaagctaa atgatgcaca agctccaaaa     180
gaattcgtgg ataacaaatt caacaaagaa caacaaaatg ctttctatga aatcttacat     240
ttacctaact taaccgaaga caacgcaat  gctttcatcc aaagcctaaa agatgaccca     300
agcgtgagca agaaatctt  agcagaagct aaaaagctaa atgatgcaca agctccaaaa     360
gaattcgtgg ataacaaatt caacaaagaa caacaaaatg ctttctatga aatcttacat     420
ttacctaact taaccgaaga caacgcaat  gctttcatcc aaagcctaaa agatgaccca     480
agcgtgagca agaaatctt  agcagaagct aaaaagctaa atgatgcaca agctccaaaa     540
gagctcgtgg ataacaaatt caacaaagaa caacaaaatg ctttctatga aatcttacat     600
ttacctaact taaccgaaga caacgcaat  gctttcatcc aaagcctaaa agatgaccca     660
agcgtgagca agaaatctt  agcagaagct aaaaagctaa atgatgcaca agctccaaaa     720
gccaccaaag ctagcaaata gctcgag                                         747

<210> SEQ ID NO 35
<211> LENGTH: 245
<212> TYPE: PRT
<213> ORGANISM: Artificial Sequence
<220> FEATURE:
<223> OTHER INFORMATION: Immunoglobulin binding protein JX04

<400> SEQUENCE: 35

Met Val Asp Asn Lys Phe Asn Lys Glu Gln Gln Asn Ala Phe Tyr Glu
1               5                   10                  15

Ile Leu His Leu Pro Asn Leu Thr Glu Glu Gln Arg Asn Ala Phe Ile
            20                  25                  30

Gln Ser Leu Lys Asp Asp Pro Ser Val Ser Lys Glu Ile Leu Ala Glu
        35                  40                  45

Ala Lys Lys Leu Asn Asp Ala Gln Ala Pro Lys Glu Phe Val Asp Asn
    50                  55                  60

Lys Phe Asn Lys Glu Gln Gln Asn Ala Phe Tyr Glu Ile Leu His Leu
65                  70                  75                  80
```

```
Pro Asn Leu Thr Glu Glu Gln Arg Asn Ala Phe Ile Gln Ser Leu Lys
                 85                  90                  95

Asp Asp Pro Ser Val Ser Lys Glu Ile Leu Ala Glu Ala Lys Lys Leu
            100                 105                 110

Asn Asp Ala Gln Ala Pro Lys Glu Phe Val Asp Asn Lys Phe Asn Lys
        115                 120                 125

Glu Gln Gln Asn Ala Phe Tyr Glu Ile Leu His Leu Pro Asn Leu Thr
    130                 135                 140

Glu Glu Gln Arg Asn Ala Phe Ile Gln Ser Leu Lys Asp Asp Pro Ser
145                 150                 155                 160

Val Ser Lys Glu Ile Leu Ala Glu Ala Lys Lys Leu Asn Asp Ala Gln
                165                 170                 175

Ala Pro Lys Glu Leu Val Asp Asn Lys Phe Asn Lys Glu Gln Gln Asn
            180                 185                 190

Ala Phe Tyr Glu Ile Leu His Leu Pro Asn Leu Thr Glu Glu Gln Arg
        195                 200                 205

Asn Ala Phe Ile Gln Ser Leu Lys Asp Asp Pro Ser Val Ser Lys Glu
    210                 215                 220

Ile Leu Ala Glu Ala Lys Lys Leu Asn Asp Ala Gln Ala Pro Lys Ala
225                 230                 235                 240

Thr Lys Ala Ser Lys
                245

<210> SEQ ID NO 36
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 36
ggagatatac atatggtaga caacaaattc aac                                33

<210> SEQ ID NO 37
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 37
gttgaatttg ttgtctacca tatgtatatc tcc                                33

<210> SEQ ID NO 38
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 38
cacaagctcc aaaagccacc aaagctagca atagctcga gcacc                    45

<210> SEQ ID NO 39
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 39
```

```
ggtgctcgag ctatttgcta gctttggtgg cttttggagc ttgtg            45
```

<210> SEQ ID NO 40
<211> LENGTH: 1443
<212> TYPE: DNA
<213> ORGANISM: Artificial Sequence
<220> FEATURE:
<223> OTHER INFORMATION: DNA encoding immunoglobulin binding protein JX05

<400> SEQUENCE: 40

```
catatggcca ccaaagctag caaagtagac aacaaattca caaagaaca caaaacgcc      60
ttctacgaaa tcctgcatct gccgaacctg accgaagaac agcgtaatgc gtttattcaa   120
agtctgaaag atgacccgag cgtgtctaaa gaaattctgg ccgaagccaa aaaactgaac   180
gatgcacagg ctccgaaagt ggataataaa tttaacaaag aacagcaaaa cgcgttctat   240
gaaattctgc atctgccgaa cctgacggaa gaacagcgca atgccttcat tcaatcactg   300
aaagatgacc cgagtgtctc caagaaaatt ctggctgaag ccaaaaaact gaatgacgcc   360
caagccccga agtggataa caaatttaat aaagaacagc aaaacgcatt ctacgaaatc   420
ctgcacctgc cgaatctgac ggaagaacag cgtaatgctt ttattcaaag cctgaaagat   480
gacccgtcag tttcgaaaga aattctggca gaggccaaaa aattaaatga cgcccaagcg   540
cctaaggtgg ataacaaatt taacaaagaa caacagaatg cctttacga aattctgcac   600
ctgccgaacc tgaccgaaga caacgcaat gcgttcatcc agtccctgaa agacgatccg   660
agcgtgtcta agaaatcct ggcggaagcg aaaaaactga cgacgcaca agcaccgaaa   720
gtagacaaca aattcaacaa agaacaacaa atgcttttct atgaaatctt acatttaccc   780
aacttaaccg aagaacaacg caatgctttc atccaaagcc taaagatga cccaagcgtg   840
agcaaagaaa tcttagcaga agctaaaaag ctaaatgatg cacaagctcc aaaagaattc   900
gtggataaca aattcaacaa agaacaacaa atgctttct atgaaatctt acatttacct   960
aacttaaccg aagaacaacg caatgctttc atccaaagcc taaagatga cccaagcgtg  1020
agcaaagaaa tcttagcaga agctaaaaag ctaaatgatg cacaagctcc aaaagaattc  1080
gtggataaca aattcaacaa agaacaacaa atgctttct atgaaatctt acatttacct  1140
aacttaaccg aagaacaacg caatgctttc atccaaagcc taaagatga cccaagcgtg  1200
agcaaagaaa tcttagcaga agctaaaaag ctaaatgatg cacaagctcc aaaagagctc  1260
gtggataaca aattcaacaa agaacaacaa atgctttct atgaaatctt acatttacct  1320
aacttaaccg aagaacaacg caatgctttc atccaaagcc taaagatga cccaagcgtg  1380
agcaaagaaa tcttagcaga agctaaaaag ctaaatgatg cacaagctcc aaaatagctc  1440
gag                                                                1443
```

<210> SEQ ID NO 41
<211> LENGTH: 477
<212> TYPE: PRT
<213> ORGANISM: Artificial Sequence
<220> FEATURE:
<223> OTHER INFORMATION: Immunoglobulin binding protein JX05

<400> SEQUENCE: 41

```
Met Ala Thr Lys Ala Ser Lys Val Asp Asn Lys Phe Asn Lys Glu Gln
 1               5                  10                  15

Gln Asn Ala Phe Tyr Glu Ile Leu His Leu Pro Asn Leu Thr Glu Glu
            20                  25                  30
```

-continued

```
Gln Arg Asn Ala Phe Ile Gln Ser Leu Lys Asp Asp Pro Ser Val Ser
         35                  40                  45

Lys Glu Ile Leu Ala Glu Ala Lys Lys Leu Asn Asp Ala Gln Ala Pro
 50                  55                  60

Lys Val Asp Asn Lys Phe Asn Lys Glu Gln Gln Asn Ala Phe Tyr Glu
 65                  70                  75                  80

Ile Leu His Leu Pro Asn Leu Thr Glu Glu Gln Arg Asn Ala Phe Ile
                 85                  90                  95

Gln Ser Leu Lys Asp Asp Pro Ser Val Ser Lys Glu Ile Leu Ala Glu
                100                 105                 110

Ala Lys Lys Leu Asn Asp Ala Gln Ala Pro Lys Val Asp Asn Lys Phe
            115                 120                 125

Asn Lys Glu Gln Gln Asn Ala Phe Tyr Glu Ile Leu His Leu Pro Asn
130                 135                 140

Leu Thr Glu Glu Gln Arg Asn Ala Phe Ile Gln Ser Leu Lys Asp Asp
145                 150                 155                 160

Pro Ser Val Ser Lys Glu Ile Leu Ala Glu Ala Lys Lys Leu Asn Asp
                165                 170                 175

Ala Gln Ala Pro Lys Val Asp Asn Lys Phe Asn Lys Glu Gln Gln Asn
            180                 185                 190

Ala Phe Tyr Glu Ile Leu His Leu Pro Asn Leu Thr Glu Glu Gln Arg
        195                 200                 205

Asn Ala Phe Ile Gln Ser Leu Lys Asp Asp Pro Ser Val Ser Lys Glu
    210                 215                 220

Ile Leu Ala Glu Ala Lys Lys Leu Asn Asp Ala Gln Ala Pro Lys Val
225                 230                 235                 240

Asp Asn Lys Phe Asn Lys Glu Gln Gln Asn Ala Phe Tyr Glu Ile Leu
                245                 250                 255

His Leu Pro Asn Leu Thr Glu Glu Gln Arg Asn Ala Phe Ile Gln Ser
            260                 265                 270

Leu Lys Asp Asp Pro Ser Val Ser Lys Glu Ile Leu Ala Glu Ala Lys
        275                 280                 285

Lys Leu Asn Asp Ala Gln Ala Pro Lys Glu Phe Val Asp Asn Lys Phe
    290                 295                 300

Asn Lys Glu Gln Gln Asn Ala Phe Tyr Glu Ile Leu His Leu Pro Asn
305                 310                 315                 320

Leu Thr Glu Glu Gln Arg Asn Ala Phe Ile Gln Ser Leu Lys Asp Asp
                325                 330                 335

Pro Ser Val Ser Lys Glu Ile Leu Ala Glu Ala Lys Lys Leu Asn Asp
            340                 345                 350

Ala Gln Ala Pro Lys Glu Phe Val Asp Asn Lys Phe Asn Lys Glu Gln
        355                 360                 365

Gln Asn Ala Phe Tyr Glu Ile Leu His Leu Pro Asn Leu Thr Glu Glu
    370                 375                 380

Gln Arg Asn Ala Phe Ile Gln Ser Leu Lys Asp Asp Pro Ser Val Ser
385                 390                 395                 400

Lys Glu Ile Leu Ala Glu Ala Lys Lys Leu Asn Asp Ala Gln Ala Pro
                405                 410                 415

Lys Glu Leu Val Asp Asn Lys Phe Asn Lys Glu Gln Gln Asn Ala Phe
            420                 425                 430

Tyr Glu Ile Leu His Leu Pro Asn Leu Thr Glu Glu Gln Arg Asn Ala
        435                 440                 445

Phe Ile Gln Ser Leu Lys Asp Asp Pro Ser Val Ser Lys Glu Ile Leu
```

```
                450              455              460
Ala Glu Ala Lys Lys Leu Asn Asp Ala Gln Ala Pro Lys
465              470              475

<210> SEQ ID NO 42
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 42
cacaagcacc gaaagtagac ctcatcggat ccc                              33

<210> SEQ ID NO 43
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 43
gggatccgat gaggtctact ttcggtgctt gtg                              33

<210> SEQ ID NO 44
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 44

Ala Thr Lys Ala Ser Lys
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 45

Ala Ser Lys Ala Thr Lys
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 46

Ala Ser Lys Ala Ser Lys
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 47

Ala Thr Lys Ala Thr Lys
```

```
<210> SEQ ID NO 48
<211> LENGTH: 6
<212> TYPE: PRT
<213> ORGANISM: Artificial Sequence
<220> FEATURE:
<223> OTHER INFORMATION: XX-UU-XX motif
<220> FEATURE:
<221> NAME/KEY: MISC_FEATURE
<222> LOCATION: (1)..(2)
<223> OTHER INFORMATION: X1 and X2 are K, S or T.
<220> FEATURE:
<221> NAME/KEY: misc_feature
<222> LOCATION: (3)..(4)
<223> OTHER INFORMATION: Xaa can optionally be any amino acid
<220> FEATURE:
<221> NAME/KEY: MISC_FEATURE
<222> LOCATION: (5)..(6)
<223> OTHER INFORMATION: X5 and X6 are K, S or T.

<400> SEQUENCE: 48

Xaa Xaa Xaa Xaa Xaa Xaa
1               5

<210> SEQ ID NO 49
<211> LENGTH: 7
<212> TYPE: PRT
<213> ORGANISM: Artificial Sequence
<220> FEATURE:
<223> OTHER INFORMATION: XXX-GA-XX motif
<220> FEATURE:
<221> NAME/KEY: MISC_FEATURE
<222> LOCATION: (1)..(3)
<223> OTHER INFORMATION: X1, X2 and X3 are A, K, S or T.
<220> FEATURE:
<221> NAME/KEY: MISC_FEATURE
<222> LOCATION: (6)..(7)
<223> OTHER INFORMATION: X6 and X7 are A, K, S or T.

<400> SEQUENCE: 49

Xaa Xaa Xaa Gly Ala Xaa Xaa
1               5
```